[19] United States Patent
Chappell

[11] Patent Number: 4,558,989
[45] Date of Patent: Dec. 17, 1985

[54] FLUID PUMP

[75] Inventor: Anthony G. Chappell, Mosman, Australia

[73] Assignee: Wellcome Australia Limited, Concord, Australia

[21] Appl. No.: 630,339

[22] Filed: Jul. 12, 1984

Related U.S. Application Data

[63] Continuation of Ser. No. 490,653, May 2, 1983, abandoned, which is a continuation of Ser. No. 144,321, Apr. 28, 1980, abandoned.

[30] Foreign Application Priority Data

May 4, 1979 [AU] Australia ............................ PD8632

[51] Int. Cl.$^4$ ........................ F04B 49/02; A61M 5/00
[52] U.S. Cl. ..................................... 417/44; 417/412; 417/478; 604/153
[58] Field of Search ............... 417/478, 412, 474, 479, 417/480, 44, 45; 604/153

[56] References Cited

U.S. PATENT DOCUMENTS

| | | | |
|---|---|---|---|
| 2,351,828 | 6/1944 | Marsh | 417/44 |
| 3,349,716 | 10/1967 | Weber | 417/478 |
| 3,620,650 | 11/1971 | Shaw | 604/123 X |
| 3,985,133 | 10/1976 | Jenkins | 604/67 |
| 4,047,844 | 9/1977 | Robinson | 417/395 X |
| 4,199,307 | 4/1980 | Jassawalla | 417/474 |
| 4,277,226 | 7/1981 | Archibald | 604/118 X |
| 4,411,652 | 10/1983 | Kramer et al. | 604/153 |

FOREIGN PATENT DOCUMENTS

1503464  7/1969  Fed. Rep. of Germany ...... 417/412

Primary Examiner—Cornelius J. Husar
Assistant Examiner—Peter M. Cuomo
Attorney, Agent, or Firm—Ladas & Parry

[57] ABSTRACT

A fluid pump device for use in conjunction with a tubular pumping chamber which is composed of an elastic material and which has a pair of spaced-apart unidirectional valves through which fluid can be passed with cyclic compression and expansion of the chamber. The pump device is intended for medical or veterinary applications and it comprises spaced-apart clamp elements between which the pumping chamber can be removably located, an electrically actuated solenoid device for effecting cyclic relative movement of the clamp elements whereby cyclic changes in the contained volume of the pumping chamber are induced when the chamber is located between the clamp elements, and electrical circuitry associated with the solenoid for energizing the solenoid at a selectable repetition rate.

6 Claims, 9 Drawing Figures

FLUID PUMP

This is a continuation of co-pending application Ser. No. 490,653 filed on May 2, 1983 which in turn is a continuation of Ser. No. 144,321 filed Apr. 28, 1980, both abandoned.

FIELD OF THE INVENTION

This invention relates to a fluid pump device for use in pumping metered quantities of fluid at a predetermined rate. The pump device has particular but nonexclusive application in the pumping (i.e. injection or extraction) of a fluid into or from an animal by way of a hypodermic-type needle, and, solely for convenience of reference, the invention is hereinafter described in the context of such application.

BACKGROUND OF THE INVENTION

The invention or extraction of fluids into or from living bodies in accurately measured quantities at specific intervals of time is an important requirement of various medical and veterinary practices. Hitherto a number of methods have been employed for this purpose; for example drip feed systems operated by gravity, intermittent intramuscular injection in bulk quantity and powdered pumping systems employing elaborate and expensive equipment.

SUMMARY OF THE INVENTION

The present invention seeks to provide a simple and inexpensive fluid pumping system which may be employed to meter relatively accurate quantities of a fluid at relatively precise intervals of time.

Thus, the present invention provides a fluid pump device for use in conjunction with a pumping chamber which is composed of an elastic material and which has a pair of spaced-apart unidirectional valves through which fluid can be passed with cyclic compression and expansion of the chamber. The pump device comprises spaced-apart clamp elements between which the pumping chamber can be located, electrically actuated means for effecting cyclic relative movement of the clamp elements, whereby cyclic changes in the volumetric capacity of the pumping chamber are induced by the clamp elements, and means for energising the electrically actuated means at a predetermined repetition rate.

PREFERRED FEATURES OF THE INVENTION

Preferably, one of the clamp elements comprises a fixed clamp element and the other comprises a movable clamp element which is connected to the electrically actuated means. Also, the electrically actuated means preferably comprises a solenoid-type actuator having an armature element to which the movable clamp element is connected or coupled. The movable clamp element may be biased in a direction away from the pumping chamber and be movable in a direction against the pumping chamber when the electrically actuated means (the solenoid) is energised, or the movable clamp element may normally be biased against the pumping chamber and be movable in a direction away from the chamber with energisation of the electrically actuated means. The latter arrangement has certain operational and/or constructional advantages over the former.

In operation of the pump device, when the movable clamp element moves in a direction against the pumping chamber it acts to reduce (i.e. compress) the effective volume of the chamber and thereby expel fluid which is located within the chamber. Conversely, when the movable clamp element moves in a direction away from the pumping chamber it allows the chamber to recover its initial volume and, with an increase in volume of the chamber, a new charge of fluid is drawn into the chamber from a source of the fluid. The new charge is then available for expulsion from the pumping chamber during the next cycle of operation of the pump device. In the context of the present invention, the term "fluid" is intended to denote a liquid.

Means preferably are provided for detecting for the presence of gas in the pumping chamber and/or for the existence of a blockage in fluid feed lines associated with the pumping chamber, the detecting means including means for disabling the electrically actuated means and for initiating a fault condition indicator. A further fault condition indicator is preferably also provided for indicating a failure in the electrically actuated means or in associated electric circuitry.

The pumping chamber which is associated with the pump device preferably comprises an elongate tube which is formed or fitted adjacent the ends thereof with unidirectional valves, the tube being formed from an elastic (i.e. resilient) material and, when in a free state, preferably having a circular cross-section. By "elastic" material is meant a material which can be deformed under the influence of a clamping force and which possesses sufficient inherent resiliency to substantially recover its initial configuration after removal of the clamping force. The material from which the tube is formed may be resilient plastics material or a natural or synthetic rubber material such as silicon rubber.

The pumping chamber may be permanently fitted to the pump device but, more preferably, is removable therefrom. Also, the pumping chamber is preferably formed as a portion of or located in a fluid feed line which is connectable at one end to a source of fluid to be pumped and, at its other end, to an intended recipient of the fluid. The source of fluid to be pumped may be contained within the pump device and be close coupled to the pumping chamber, or it may be located remote from the pump device and be connected to the pumping chamber by a suitable length of feed line. The end of the feed line which is intended to be connected with a receiver of the pumped fluid is preferably fitted with a hypodermic-type needle.

The pump device may be constructed on a small scale, so that it might conveniently be strapped to a person's body or be fitted in a person's pocket, to permit periodic injections to be administered automatically to the person. Alternatively, the pump device may be constructed on a larger scale and normally be sited adjacent a hospital bed or the like. In either or any case, the device in accordance with the invention is intended predominantly for the purpose of administering metered quantities of fluid to a person (or animal) at a predetermined rate. The quantity of fluid administered during each cycle of the pumping device is determined by the volumetric capacity of the pumping chamber and/or by the degree of compression applied to the chamber, and the rate of administration of the fluid is determined by the pumping repetition rate. Preferably the pumping repetition rate is selectively variable and the degree of compression applied to the pumping chamber is selectively variable.

Electrical energy for the device may be obtained from batteries located within the device or from a main supply, depending upon the intended purpose of individual such devices. When power is derived from in-built batteries, the batteries are preferably of a rechargeable type and means are provided to permit connection of a battery charger to the batteries.

The invention will be more fully understood from the following description of two embodiments of the fluid pump device, the description being given by way of example and with reference to the accompanying drawings.

DETAILED DESCRIPTION OF THE INVENTION

Figure 1:
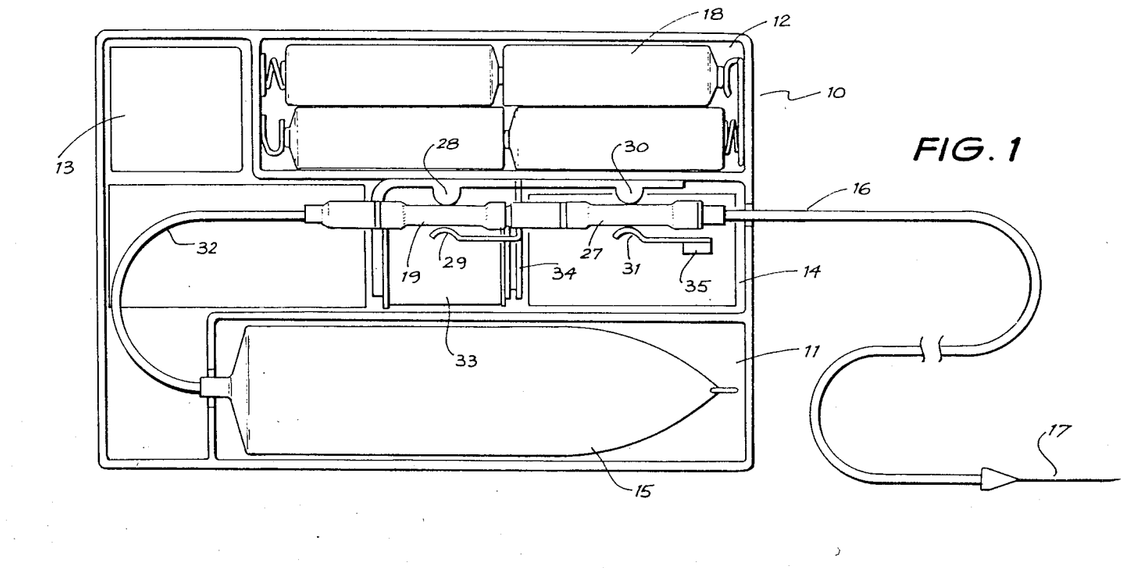
FIG. 1 shows a plan view of a first fluid pump device which incorporates its own source of fluid to be pumped by the device.
Figure 2:
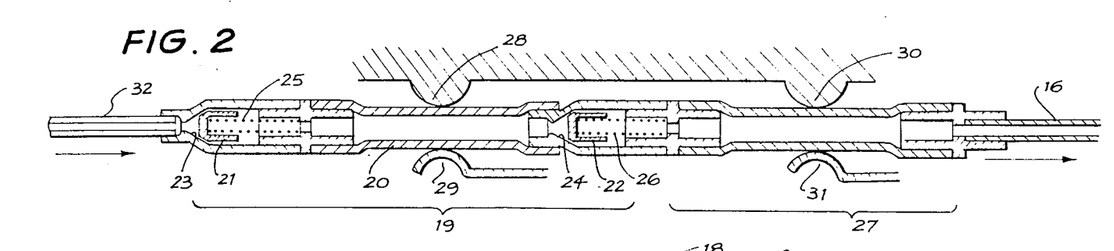
FIG. 2 shows, on an enlarged scale, a sectional view of a pumping chamber which is incorporated in the device of FIG. 1.

The fluid pump device as shown in FIGS. 1 and 2 comprises a housing 10 which is partitioned to provide four separate compartments 11, 12, 13 and 14. The compartment 11 houses a container 15 of fluid which is to be pumped into and from a fluid feed line 16 which is coupled to a hypodermic-type needle 17. The needle is intended to be inserted into a patient to whom the fluid is to be administered. The container 15 is formed from an elastic or deformable material, so that its volume will reduce as fluid is withdrawn and so as to avoid the creation of a partial vacuum within the container with extraction of its contents.

The compartment 12 houses batteries 18 which provide electrical energy to the below mentioned elements of the device, the compartment 13 contains electrical circuitry associated with the device, and the compartment 14 contains a pumping chamber 19.

The pumping chamber 19 (which is illustrated in greater detail in FIG. 2) comprises an elongate tube 20 which is formed from an elastic material (e.g. silicon rubber) and which is fitted at both ends with unidirectional valve members 21 and 22. The valve members are normally spring biased against respective valve seats 23 and 24 by helical compression springs 25 and 26.

A pulse detector chamber 27 is also located within the compartment 14, such chamber being constructed in much the same manner as the pumping chamber 19 but not being fitted with valve members.

The two chambers 19 and 27 are removably positioned within the compartment 14 between respective clamp elements 28, 29 and 30, 31, and the pumping chamber is connected to the fluid container 15 by a fluid delivery line 32. The pulse detector chamber 27 is connected with the fluid line 16.

Also located within the compartment 14 is a solenoid device 33 which includes a pivotably mounted armature 34. The armature is connected to the movable clamp element 29 and, when the solenoid is energised, the clamp element 29 acts against the pumping chamber 19 to effect compression of the tube 20. When the clamping force is applied to the tube 20 the contained volume of the pumping chamber is reduced and fluid within the pumping chamber is expelled past the valve member 22 and into the pulse detector chamber 27. At the same time, increased pressure within the pumping chamber 19 holds the valve member 21 in a closed position. Then, when the solenoid 33 is de-energised, the movable clamp element 29 moves in a direction away from the pumping chamber and the chamber is permitted to resume its original volumetric capacity, this being achieved by virtue of the inherent resiliency of the tube 20. As the volume of the chamber increases and the pressure within the chamber drops, the valve member 22 is closed and a new charge of fluid is drawn into the pumping chamber from the source 15 by way of the valve member 21. Once the pumping chamber 19 has been primed, successive energisations of the solenoid 33 results in successive pulses of fluid being pumped through the device.

The clamp element 31 is a movable element and is permanently biased against the elastic tube 34 of the pulse detector chamber 27. Also, the clamp element 31 is coupled to a transducer 35 which detects for movement of the clamp element 31 and which provides an electrical output to electric logic circuitry. Such circuitry is not shown in the drawings but is contained within the compartment 13 and operates in the following manner:

If air is contained within the pumping chamber 19, when the solenoid 33 is actuated it will function only to compress the air and, with appropriate force applied to the valve member 22 by the spring 26, the air will not be pumped into the chamber 27. Thus, the clamp element 31 will not be moved outwardly to any significant extent (as it would otherwise be if a pulse of fluid were to be pumped into the chamber 27), and the absence of significant movement of the clamp element 31 will result in a zero or low output from the transducer 35. Such output is fed to an alarm device (not shown) by the logic circuitry to indicate the existence of an air bubble in the pumping chamber and to disabling circuitry associated with the solenoid energisation circuit.

If a blockage occurs in the feed line 16, when the solenoid is actuated to pump fluid into the pulse detector chamber 27 the fluid will be subjected to forward resistance and will tend to expand the tube 34 of the chamber 27 to an abnormal extent and thereby cause greater-than-normal movement of the clamp element 31. Such movement will be imparted to the transducer 35 and will result in a high level output signal from the transducer. The high level output signal will then be fed to the logic circuitry to indicate the existence of a line blockage and to the disabling circuitry associated with the solenoid.

Reference is now made to FIGS. 3 to 9 of the drawings and hence to the second embodiment of the pump device.

Figure 3:
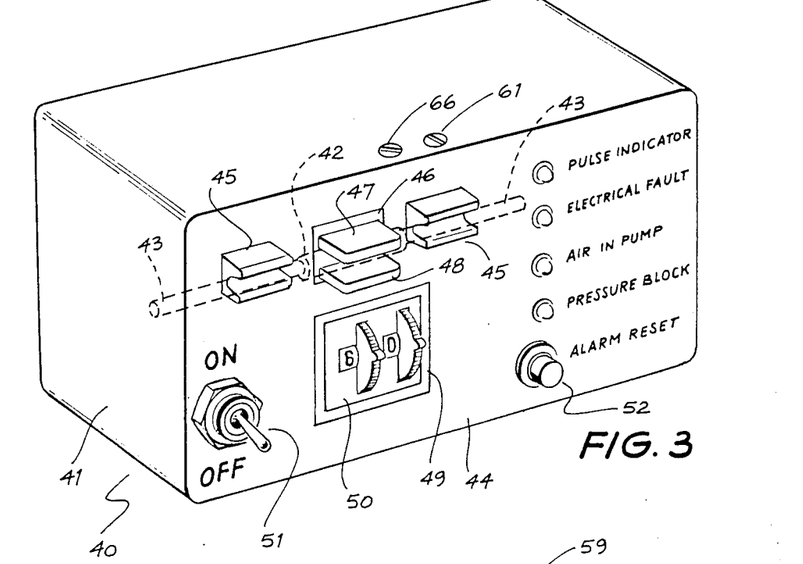
FIG. 3 shows a perspective view of a second fluid pump device to which a pumping chamber (which is connectable to a remote source of fluid) can be fitted.
Figure 4:
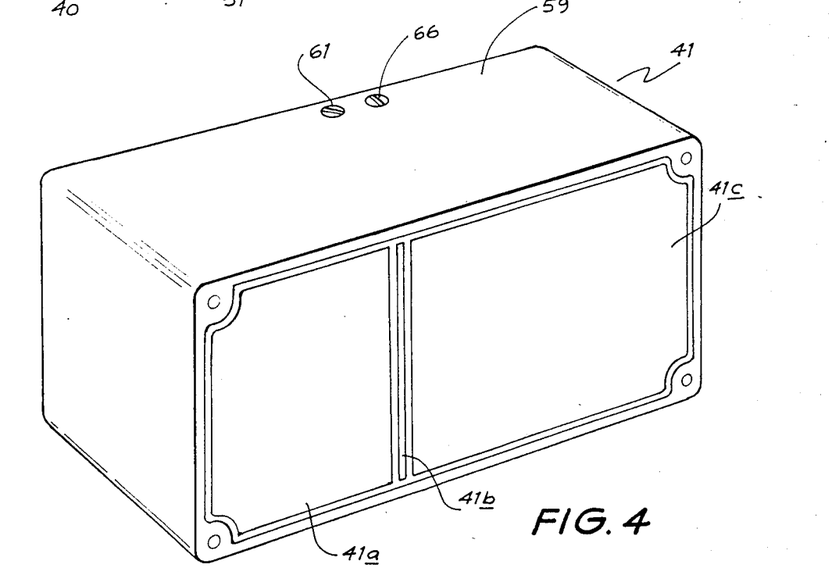
FIG. 4 shows a reverse side view of the device of FIG. 3 with a rear cover plate removed.

In this case, the pump device comprises a casing 40 having an oblong housing 41 and a removable rear cover which is absent from the casing as shown in FIG. 4. The casing 40 does not house a pumping chamber or fluid source (in contrast with the previously described embodiments) but, rather, a pumping chamber 42 and associated feed line 43 is mounted to the front face 44 of the casing as indicated by the dotted outline in FIG. 3.

As shown in FIG. 3, two generally U-shaped support elements 45 are fitted or moulded onto the front face of the casing 41 and are used to hold the feed line 43 in situ. Also, a first opening 46 is formed in the face of the casing and through which fixed and movable clamp elements 47 and 48 project.

A second opening 49 is also formed in the front face 44 of the casing and through which a pulse rate selector device 50 projects. The selector device 50 is connected with electrical circuitry which is to be hereinafter described and it has elements which can be turned manually to "dial-up" a required number of "pulses per minute" to be delivered to a solenoid which is to be hereinafter referred to. As illustrated, the selector device is set to initiate 60 energisations per minute of the solenoid. Additionally, a main ON-OFF switch 51 is mounted to the front face 44 of the casing, as are a series of four indicator lamps. The lamps illuminate to indicate the conditions which are designated by the indicia which is marked or inscribed on the front face of the casing as shown in FIG. 3. Finally, the front face of the casing is fitted with an alarm reset (push-button) switch 52 as indicated in FIG. 3.

Within the casing 41 and as viewed in FIG. 4 are a battery compartment 41a, two printed circuit boards 41b and 41c and electric circuit components (not specifically shown) which are mounted to the printed circuit boards. Additionally, located behind the circuit board 41b and as shown in FIG. 5 are the selector device 50, the switch 51 and a solenoid 53.

Figure 5:
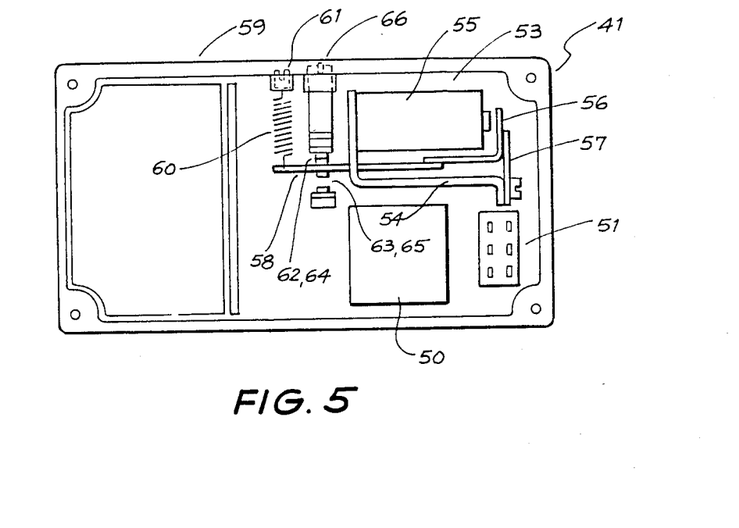
FIG. 5 shows an interior view of the device of FIG. 3 (as viewed in the direction of FIG. 4), with certain components of the device removed.
Figure 6:
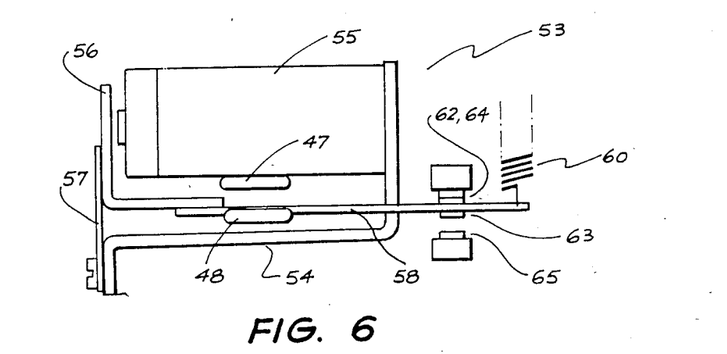
FIG. 6 shows a solenoid component of the pump device of FIG. 3, the solenoid being shown removed from the device housing.

As shown in FIGS. 5 and 6, the solenoid comprises a yoke 54, a coil 55 which is mounted to the yoke and an L-shaped armature 56 which is pivotably mounted to the yoke by a resilient flat plate 57. Also, the fixed clamp element 47 is mounted to or extends from the yoke 54 and the movable clamp element 48 is mounted to the armature, both of the clamp elements projecting through the opening 46 in the front face 44 of the casing to the position shown in FIG. 3. When the solenoid is energised, the armature 56 of the solenoid moves to cause the movable clamp element 48 to move in a direction away from the fixed clamp element 47.

An extension arm 58 of the armature is connected to one wall 59 of the casing by a helical tension spring 60, and the spring acts normally to bias the armature 56 to an open position and hence to bias the movable clamp element 48 in a direction toward the fixed clamp element 47. Thus, successive energisation and de-energisation of the solenoid causes the pumping chamber 42 (FIG. 3) to be expanded and compressed between the clamp elements 47 and 48.

A screw connection 61 is made between the spring 60 and the housing wall 59 to permit adjustment of the effective length of the spring and, therefore, to permit adjustment of the force exerted on the extension arm 58 by the spring.

A pair of oppositely directed moving contacts 62 and 63 are formed on the extension arm 58 for contacting fixed contacts 64 and 65 respectively. The contacts 62 and 64 are normally closed (when the solenoid is not energised) and the contacts 63 and 65 are normally open. The position of fixed contact 64 can be adjusted by a screw connector 66.

Figure 7:
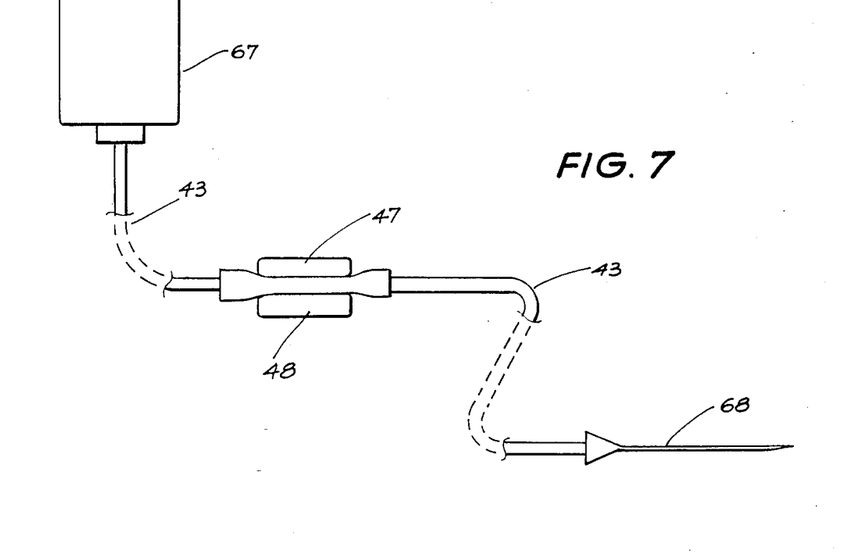
FIG. 7 shows a fluid source, pumping chamber and fluid feed line arrangement which is connectable with the device of FIG. 3.

The pumping chamber 42 and feed line 43 are shown in FIG. 7 in association with other components which might be considered collectively as forming a patient circuit. Thus, the pumping chamber 42 is connected (or connectable) to a source 67 of injectable fluid and to a hypodermic type needle 68 by the feed line 43.

Figure 8:
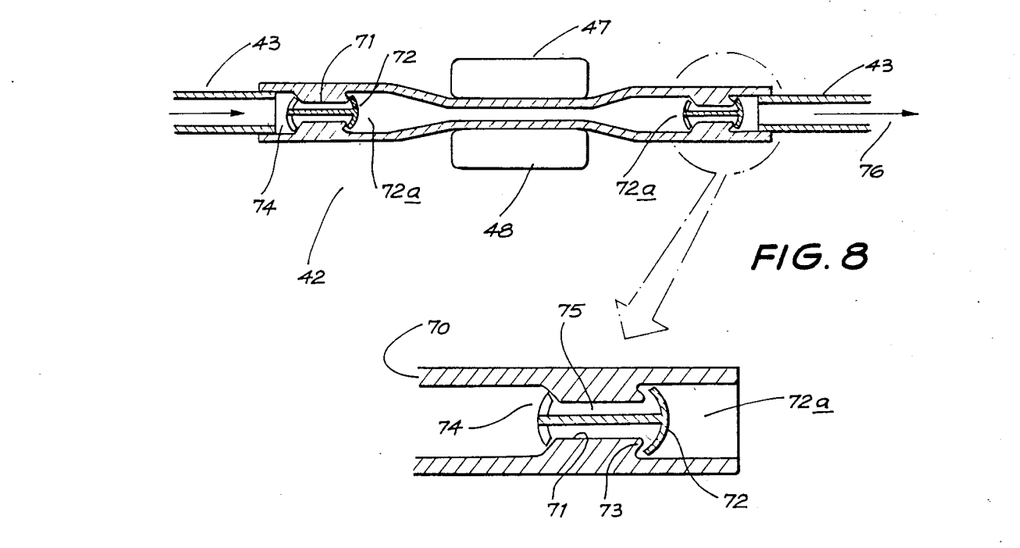
FIG. 8 shows a detailed sectional elevation view of the pumping chamber portion of the arrangement shown in FIG. 7.

As best seen from FIG. 8, the pumping chamber 42 comprises a tube 70 which is formed from an elastic material (as in the case of the previously described embodiment) and the tube is formed adjacent each end thereof with a throat portion 71. A valve member 72a is located in each of the throats 71. Each valve member has a head 72 which normally closes against a seat 73, a cruciform-shaped tail 74 through which fluid may pass and a connecting stem 75. The two valve members are formed from a resilient material and they function to permit fluid to pass only in the direction indicated by the arrow 76. Thus, when the solenoid is energised and the clamp element 48 moves away from element 47, the pumping chamber is expanded to permit fluid flow into the chamber, and, when the solenoid is de-energised and the clamp element 48 moves toward the element 47, the pumping chamber is compressed so as to expel contained fluid. The spacial relationship of the clamp elements 47 and 48 is adjusted so that even when the solenoid is energised a small degree of clamping is applied to the pumping chamber 42.

Figure 9:
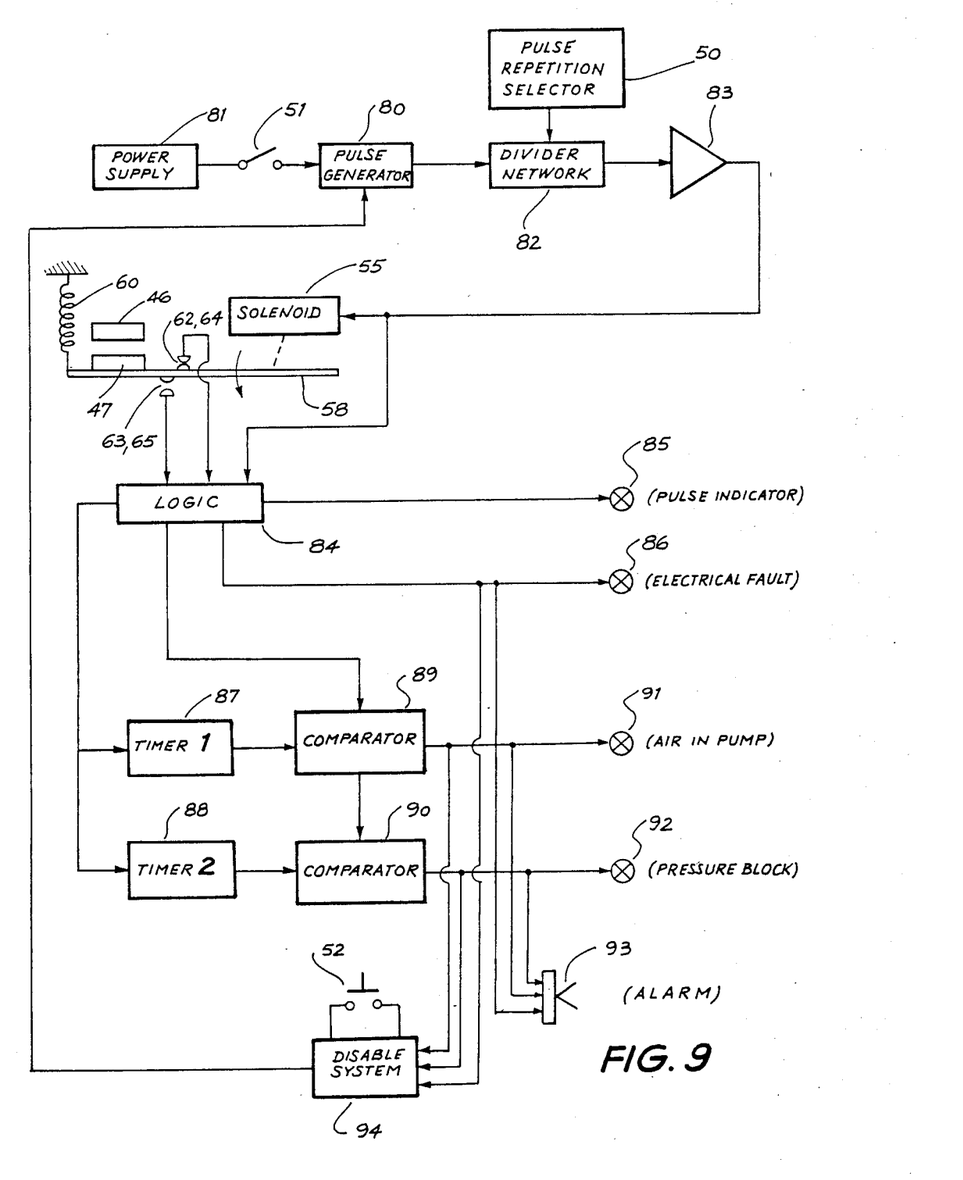
FIG. 9 shows a schematic circuit diagram of electrical components which are incorporated in the pump device of FIG. 3.

A description is now provided in respect of the use and operation of the pump device, the description being given with reference to FIGS. 3 to 8 and, where appropriate, to the circuit diagram of FIG. 9.

Firstly, a pre-sterilised "patient circuit" comprising the pumping chamber 42 feed line 43 and hypodermic needle 68 is connected to the source 67 of injectable material.

Secondly and prior to fitting of the "patient circuit" to the fluid pump device, the pumping chamber 42 is operated manually so as to pump fluid into the pumping chamber and feed line and so as to expel all air from the patient circuit. This operation is necessary before fitting the patient circuit to the pump device because such device will not in fact operate to clear the system of air, whilst any air exists in the system, the pump device will indicate a fault condition. This because the pumping chamber does not have its contained volume reduced to zero during successive operations of the solenoid whereas this operation can be performed manually. In fact, the pump device is designed such that total compression of the pumping chamber is not effected during normal operation of the device, so that detection might be made for the presence of any unwanted air bubbles which may enter the pumping chamber.

Thirdly, after clearing all air from the patient circuit, this being indicated when fluid is expelled from the hypodermic needle 68, the pumping chamber 42 is mounted to the pump device as indicated in FIG. 3.

Fourthly, the device is then switched on. This operation does not itself result in energisation of the solenoid 53 but, to enable a check to be made on the alarm circuits, it should cause illumination of the fault condition indicator lamps (FIGS. 3 and 9). Also, an audible alarm is initiated. A logic circuit which is shown in FIG. 9 and which is hereinaftered referred to controls these functions.

Fifthly, the alarm reset button 52 is pressed and, if no faults exist in the system, successive energisations of the solenoid will occur to result in the pumping of fluid through the patient circuit.

Sixthly, the device is switched-off and a desired infusion rate (i.e. energising pulse repetition rate to the solenoid) is selected by "dialing-up" the appropriate number on the selector device 50. Typically, the pulse repetition rate may be selected somewhere in the range of one pulse per minute to one hundred pulses per minute.

Thereafter, the hypodermic needle is inserted in the patient and the pump device is again switched-on, following the procedures of steps numbered four and 5.

Although not shown in the drawings, means such as a "total" pulse counter may be incorporated in the pump device to automatically switch-off the device following the occurrence of a predetermined number of energisations of the solenoid. In any case, if the device is not switched-off before the source 67 is depleted of all fluid, the pump will automatically switch-off because a fault condition (i.e. no fluid in the pumping chamber 42) will be sensed, as hereinafter mentioned.

The operation of the pump device under fault conditions will be described below with reference to the description which is now given in respect of the electrical circuitry associated with the device and as shown in FIG. 9 of the drawings.

A pulse generator 80 is powered from the power supply (batteries) 81 by way of the switch 51. The pulse generator produces a train of square-wave pulses, with each pulse having a width of approximately 40 ms. However this pulse width may be different in pump devices which are intended for different applications or it may be selectively variable.

The output from the pulse generator is applied to a divider network 82 which is controlled to provide a selected pulse repetition rate output by the selector device 50 (see also FIG. 1). The pulse repetition rate might typically be selected to fall within the range of 1 pulse per minute to 100 pulses per minute. The output of the divider is amplified in a driver 83 and the output of the driver is applied to the solenoid coil 55.

A logic circuit 84 which is controlled by pulses from the pulse generator has input derived rom the normally open and normally closed contacts 64 and 65, and one output from the logic circuit is employed to illuminate lamps 85 with each excitation pulse applied to the solenoid. Alternatively and in the event that the solenoid is not energised, another output will be derived from the logic circuit to illuminate the lamp 86.

When the solenoid 55 is energised the clamp element 47 is moved in a direction away from the element 46, the normally closed contacts 62, 64 open and the normally open contacts 63, 65 close. Thereafter, when the solenoid is de-energised the spring 60 causes movement of the clamp element 47 toward the element 46 and re-establishment of the normally open and normally closed contact relationship. The time occupied in restoration of this relationship is measured by timers 87 and 88 to provide an indication of possible fault conditions in the system.

If air is present in the pumping chamber 42 or if the feed line 43 to the pumping chamber is blocked or if no fluid is available for delivery to the pumping chamber or if the pumping chamber is not properly inserted between the clamp elements 46 and 47, a lower-than-normal resistance will be exerted against closure of the clamp element 47 by the pumping chamber 42 and the element 47 will close more quickly than a predetermined time period T. Conversely, if a block occurs in the feed line 43 to the patient, a pressure build-up will occur in the pumping chamber 42 and a greater-than-normal resistance will be exerted against closure of the clamp element 47. Thus the clamp element 47 will close more slowly than the predetermined time interval T.

The timers 87 and 88 function, in effect, to measure the closing time of the clamp element 47 and the time-related output signals from the timers 87 and 88 are compared with reference signals in comparators 89 and 90. If the closing time for the clamp element 47 is less than the predetermined time T the indicator lamp 91 will be illuminated, and if the closing time for the clamp element is greater than the predetermined time T the indicator lamp 92 will be illuminated.

Illumination of any one of the lamps 86, 91 or 92 results also in a signal being applied to an audible alarm 93. Additionally, the existence of a fault condition causes disabling of the pulse generator 80 by way of disabling system 94.

As above mentioned, at the time of initial switch-on of the pump device, the logic circuitry causes excitation of the fault indicating lamps, to enable a check to be made on the operation of such lamps, and the alarm reset push button 52 is provided for resetting the disabling network and initiating operation of the pulse generator if no fault condition does in fact exist in the system.

I claim:

1. A fluid pump device for use in conjunction with a pumping chamber which is composed of an elastomeric material, which has a pair of spaced-apart unidirectional valves through which fluid can be pumped with cyclic compression and expansion of the chamber and which extends toward its full volumetric capacity following removal of a compressive force, the fluid pump device comprising:
    (a) spaced-apart clamp elements between which the pumping chamber (is in use and) is removably located, one end of said pumping chamber being connectable to a source of fluid to be pumped and the other end of said pumping chamber being connected to a hypodermic-type needle by way of a fluid feed line (so that said needle establishes a firm connection for administering said fluid),
    (b) means for biasing the clamp elements in a direction one toward the other, whereby the clamp elements function to compress and reduce the contained volume of the pumping chamber,
    (c) electrically actuated means which when energized effect relative movement of the clamp elements in a direction one away from the other, whereby the pumping chamber is permitted to expand in a direction toward its full volumetric capacity, and when de-energized permits movement of the clamp elements toward one another under the influence of said biasing means,
    (d) means for energizing the electrically actuated means at a predetermined rate whereby cyclic changes in the volumetric capacity of the pumping chamber occur with periodic energization and de-energization of the electrically actuated means, and (e) timing means for timing the period of relative movement of the clamp elements toward one another following the de-energization of the electrically actuated means and for providing a fault condition indicating signal if the timed period is less than a predetermined first time interval, this being indicative of an excessively low back pressure in the pumping chamber, or is greater than a predetermined second time interval which is indicative of an excessively high back pressure in the pumping chamber.

2. A fluid pump device as claimed in claim 1 wherein one of the clamp elements comprises a fixed clamp element and the other clamp element comprises a movable clamp element which is connected to the electrically actuated means.

3. A fluid pump device as claimed in claim 1 wherein the electrically actuated means comprises a solenoid operated device.

4. A fluid pump device as claimed in claim 1 and including a casing which houses the electrically actuated means and the means for energising the electrically actuated means.

5. A fluid pump device as claimed in claim 1 or claim 2 wherein the means for energising the electrically actuated means include a pulse generator for generating excitation pulses for delivery to the electrically actuated means.

6. A fluid pump device as claimed in claim 5 wherein a divider network is located between the pulse generator and the electrically actuated means, and wherein a pulse repetition rate selector is connected to the divider network for selectively determining the pulse repetition rate of output pulses from the divider network.

* * * * *